(12) United States Patent
Zimmer (10) Patent No.: US 9,973,854 B1
(45) Date of Patent: May 15, 2018

(54) ELECTRONIC HEADSET

(71) Applicant: Trent Zimmer, Houma, LA (US)

(72) Inventor: Trent Zimmer, Houma, LA (US)

( * ) Notice: Subject to any disclaimer, the term of this patent is extended or adjusted under 35 U.S.C. 154(b) by 0 days. days.

(21) Appl. No.: 15/813,056

(22) Filed: Nov. 14, 2017

Related U.S. Application Data (60) Provisional application No. 62/423,069, filed on Nov. 16, 2016.

(51) Int. Cl.
  *H04R 5/033* (2006.01)
  *H04R 1/10* (2006.01)
  *A61F 11/14* (2006.01)

(52) U.S. Cl.
  CPC ......... *H04R 5/0335* (2013.01); *H04R 1/1008* (2013.01); *A61F 11/14* (2013.01)

(58) Field of Classification Search
  None
  See application file for complete search history.

(56) References Cited

U.S. PATENT DOCUMENTS

| | | | | |
|---|---|---|---|---|
| 4,302,635 A * | 11/1981 | Jacobsen | ............. | H04R 1/1058 381/371 |
| 5,056,161 A * | 10/1991 | Breen | .................. | H04R 1/1066 2/209 |
| 9,838,776 B2 * | 12/2017 | Broadley | ............. | H04R 1/1066 |
| 2002/0003889 A1 | 1/2002 | Fischer | | |
| 2004/0218776 A1 * | 11/2004 | Rolla | ..................... | A42B 3/166 381/374 |
| 2006/0147052 A1 | 7/2006 | Wikel et al. | | |
| 2008/0175406 A1 * | 7/2008 | Smith | .................. | H04R 1/1066 381/87 |
| 2008/0298622 A1 * | 12/2008 | Lee | ....................... | H04R 1/1066 381/378 |
| 2010/0310093 A1 * | 12/2010 | Semcken | ............. | H04R 1/1058 381/104 |
| 2014/0259287 A1 | 9/2014 | Waters et al. | | |
| 2017/0264984 A1 * | 9/2017 | Pelland | .................... | H04R 1/06 |

* cited by examiner

*Primary Examiner* — Paul Huber
(74) *Attorney, Agent, or Firm* — Asgaard Patent Services, LLC; F. Wayne Thompson, Jr.

(57) ABSTRACT

Implementations of an electronic headset are provided. In some implementations, the electronic headset may be configured to be worn on the head of a user. In some implementations, the electronic headset may be configured so that two earcups can be removably and/or rotatably coupled to a headband thereof. In some implementation, the electronic headset may be configured to power attached electronic earcups and/or other electrically powered accessories (e.g., a light, etc.) conductively coupled thereto. In some implementations, an electronic headset may comprise a headband having a mounting bracket on each end thereof, two earcup mounting hubs, and an electronic circuitry comprising a power source. In some implementations, each earcup mounting hub may be configured to conductively interface with a mounting bracket when coupled thereto. In this way, the electronic earcups may be powered by the electronic headset.

28 Claims, 8 Drawing Sheets

SECTION A-A

SCALE 1:1

ELECTRONIC HEADSET

CROSS REFERENCE TO RELATED APPLICATION

This application claims the benefit of U.S. Provisional Application Ser. No. 62/423,069, which was filed on Nov. 16, 2016, and is incorporated herein by reference in its entirety.

TECHNICAL FIELD

This disclosure relates to implementations of an electronic headset.

BACKGROUND

Headsets are routinely used in both military and law enforcement settings to protect a user's hearing and to facilitate hands-free communication. Some headsets include earcups configured to cover a wearer's ears that are connected by a headband or other headpiece connecting structure (e.g., a helmet). Some earcups include an electronic sound dampening device to protect the wearer's hearing, while other earcups may be passive and not require any electronic aid to provide hearing protection.

Modern military and law enforcement users often find the need to power accessory devices that enhance their operational capabilities (e.g., a light, a global positioning system (GPS), a thermal imager, a night vision device (NVD), etc.). Currently, there is no uniform means to power one or more accessory devices using a single conductively connected power source or to extend the run time of an electrically powered accessory device by augmenting the onboard power source using a secondary conductively connected power source.

Accordingly, it can be seen that needs exist for the electronic headset disclosed herein. It is to the provision of an electronic headset configured to address these needs, and others, that the present invention in primarily directed.

SUMMARY OF THE INVENTION

Implementations of an electronic headset are provided. In some implementations, the electronic headset may be configured to be worn on the head of a user. In some implementations, the electronic headset may be configured so that two earcups can be removably and/or rotatably coupled to a headband thereof. In some implementation, the electronic headset may be configured to power attached electronic earcups (e.g., the earcups of a Peltor ComTac series headset) and/or other electrically powered accessories (e.g., a light, a global positioning system (GPS), a thermal imager, a night vision device (NVD), etc.) conductively coupled thereto.

In some implementations, an electronic headset may comprise a headband having a mounting bracket on each end thereof, two earcup mounting hubs, and an electronic circuitry comprising a power source. In some implementations, each earcup mounting hub may be configured to removably and/or rotatably couple to a mounting bracket positioned on each end of the headband. In this way, each earcup may be removably and/or rotatably secured to the headband of an electronic headset. In some implementations, each earcup mounting hub may be configured to conductively interface with a mounting bracket when coupled thereto. In this way, the electronic earcups may be powered by the electronic headset.

In some implementations, a curved bridle may extend between the first mounting bracket and the second mounting bracket. In some implementations, one or more wires may be secured on and/or supported by the curved bridle. In some implementations, the one or more wires may be configured to conductively connect the first mounting bracket and the second mounting bracket to, at least, the power source of the electronic headset.

In some implementations, each earcup mounting hub may further comprise an accessory mount that includes a mounting interface thereon configured to receive therein a portion of an accessory adaptor (e.g., a MIL-STD-1913 rail piece) to which an accessory (e.g., a light, a global positioning system (GPS), etc.) may be attached. In some implementations, an accessory may be configured to secure directly to a mounting interface without an accessory adaptor. The general features and advantages of the mounting interface and compatible accessory adapters are described in U.S. Pat. No. 9,488,446, filed on Aug. 12, 2014, entitled "MULTIPLE ACCESSORY GUN MOUNT", by Trent Zimmer, which is also owned by the present applicant and is hereby expressly incorporated by reference as if fully set forth herein.

In some implementations, the power source (e.g., a battery pack) of the electronic circuit may be conductively connected to the first earcup and/or the second earcup via the conductive interface that exist between a coupled mounting bracket and mounting hub. In some implementations, an electrically powered accessory (e.g., a light, a global positioning system (GPS), a thermal imager, a night vision device (NVD), etc.) may be conductively connected to the power source via a power socket(s) of an earcup mounting hub. In some implementations, the power source may also be configured to act as a junction and provide one or more additional power sockets to which electrically powered accessories may be conductively coupled.

In some implementations, the housing of the first power source may be configured to mount on, or be permanently affixed to, the headband of the electronic headset.

In some implementations, the electronic circuit may further comprise a second power source (e.g., a battery pack). In this way, additional power may be provided to any electrically powered accessories conductively connected to the electronic headset. In some implementations, the second power source may be connected to the electronic circuit of an electronic headset via a suitably configured electronic cable. In this way, the second power source may be remotely positioned relative to the electronic headset (e.g., carried in the pocket of a user).

In some implementations, the mounting brackets of an electronic headset may be configured for use with a helmet, instead of a headband. In some implementations, each mounting bracket may be secured to a suitable interface (e.g., a rail system) positioned on each side of the helmet. In some implementations, each mounting bracket may include a back plate configured to be received within the rail channel of a helmet rail system. In some implementations, the back plate may be adjustably secured to the rear side of a mounting bracket. In this way, the back plate may be used to clamp a mounting bracket to the rail channel of a helmet rail system.

These and other aspects, features, and advantages of the invention will be understood with reference to the drawing figures and detailed description herein, and will be realized by means of the various elements and combinations particularly pointed out in the appended claims. It is to be understood that both the foregoing general description and the following brief description of the drawings and the detailed

DETAILED DESCRIPTION

Figure 1:
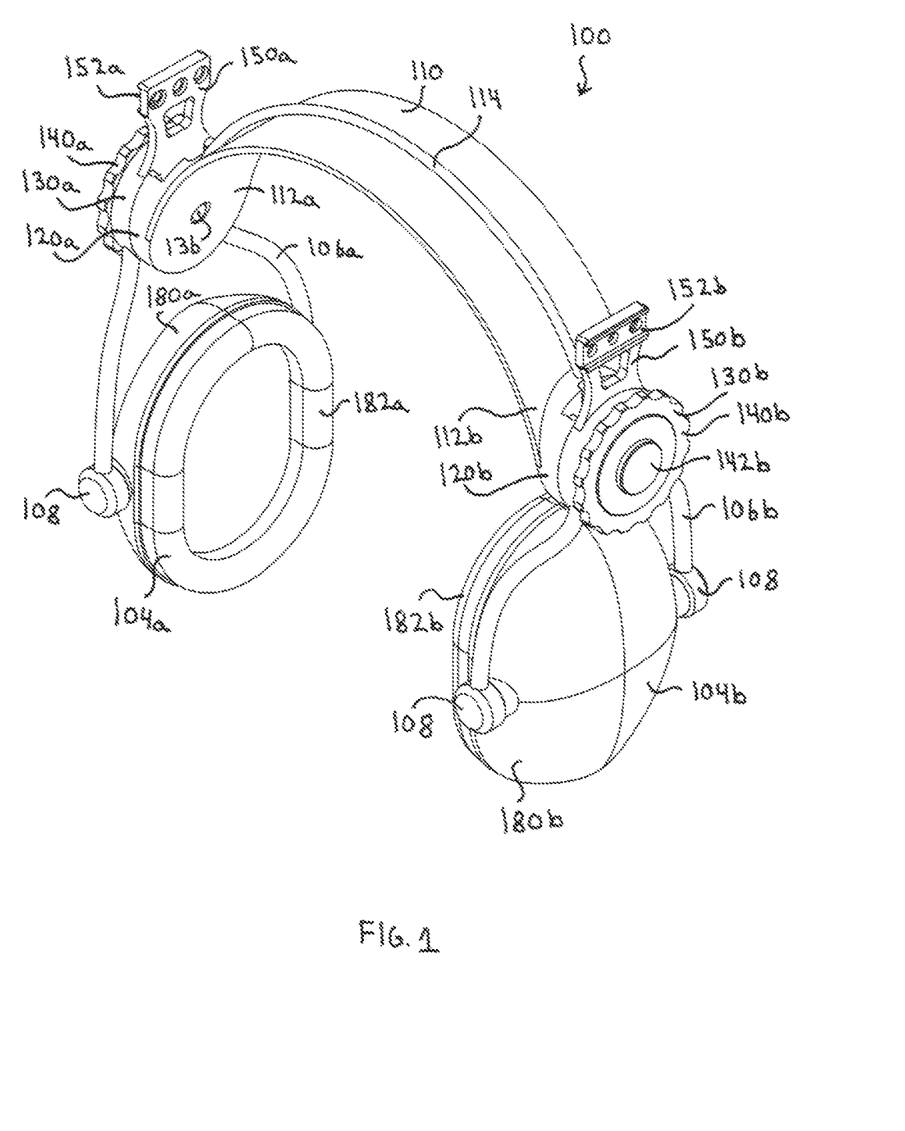
FIG. 1 illustrates an example implementation of an electronic headset according to the principles of the present disclosure.

FIG. 1 illustrates an example implementation of an electronic headset 100 according to the principles of the present disclosure. In some implementations, the electronic headset 100 may be configured to be worn on the head of a user and thereby used to position an earcup over each ear of the user. In some implementations, the electronic headset 100 may be configured so that two earcups 104a, 104b can be removably and/or rotatably coupled to a headband 110 thereof. In some implementation, the electronic headset 100 may be configured to power attached electronic earcups (e.g., the earcups of a Peltor ComTac series headset) and/or other electrically powered accessories (e.g., a light, a global positioning system (GPS), a thermal imager, a night vision device (NVD), etc.) conductively coupled thereto (see, e.g., FIG. 5).

Figure 5:
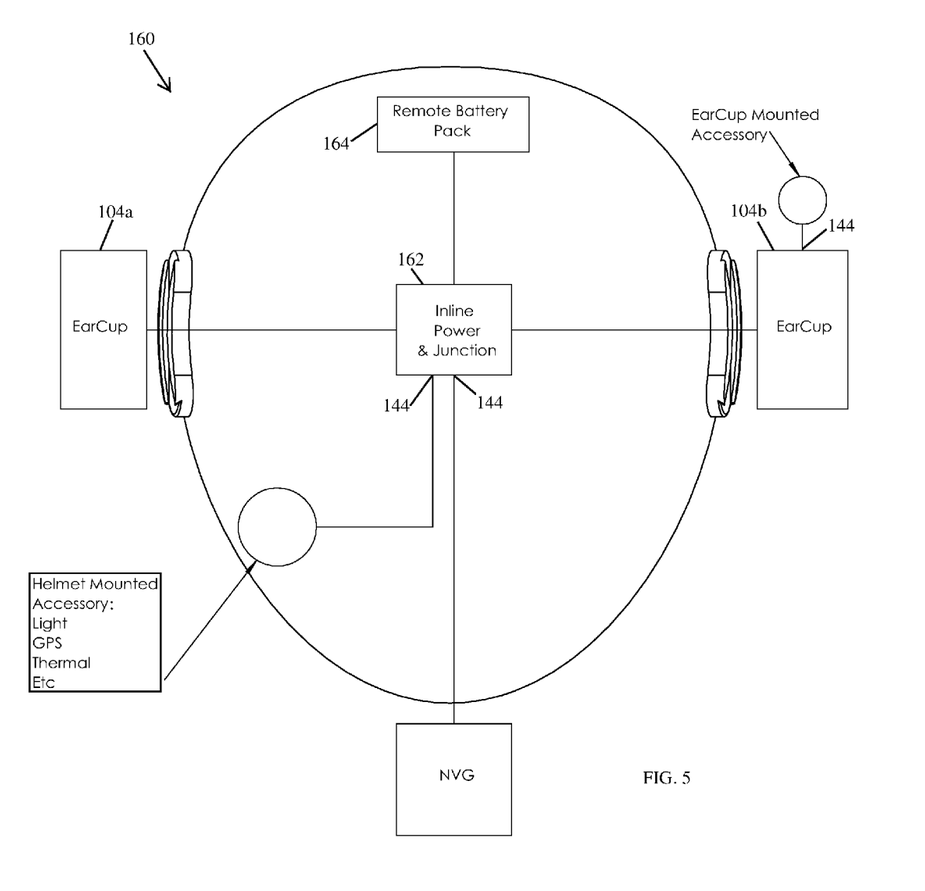
FIG. 5 illustrates an example electronic circuit used to power electronic earcups and/or other electrically powered accessories conductively coupled to the electronic headset according to the principles of the present disclosure.

As shown in FIGS. 1 and 5, in some implementations, an electronic headset 100 may comprise a headband 110 having two mounting brackets 120a, 120b (collectively mounting brackets 120) thereon, two earcup mounting hubs 130a, 130b (collectively mounting hubs 130), and an electronic circuitry 160 comprising a power source 162. In some implementations, each earcup mounting hub 130a, 130b may be configured to removably and/or rotatably couple to a mounting bracket 120a, 120b on the headband 110. In this way, each earcup 104a, 104b (collectively earcups 104) may be removably and/or rotatably secured to the headband 110 of an electronic headset 100. In some implementations, each earcup mounting hub 130a, 130b may be configured to conductively interface with a mounting bracket 120a, 120b when coupled thereto. In this way, the electronic earcups 104 may be powered by the electronic headset 100.

Figure 3A:
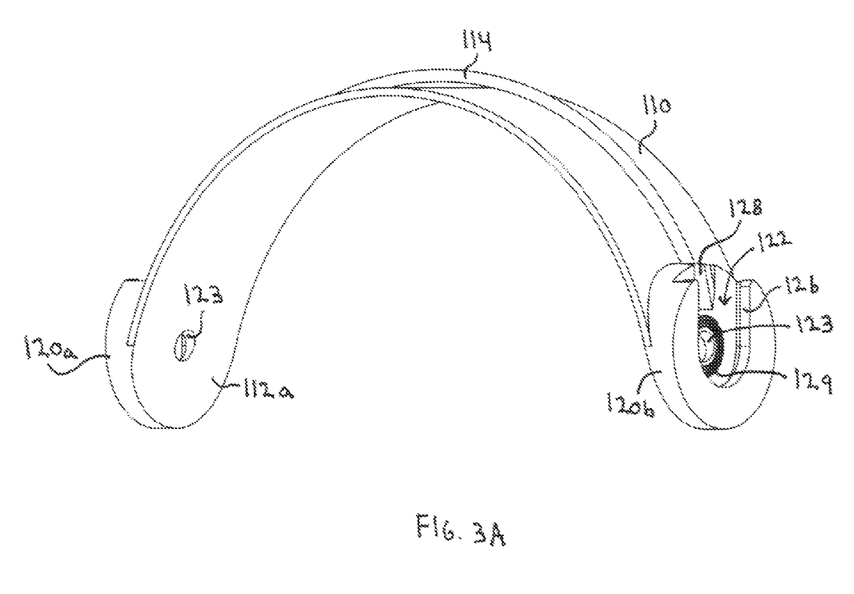
FIGS. 3A-3C illustrate an example headband of the electronic headset according to the principles of the present disclosure.

As shown in FIGS. 1 and 3A, in some implementations, the headband 110 may be curved to fit on the crown of a wearer's head. In some implementations, the first mounting bracket 120a and the second mounting bracket 120b may be positioned on a first end 112a and a second end 112b, respectively, of the headband 110 (see, e.g., FIG. 3A). In some implementations, the headband 110 may be manufactured from spring steel. In some implementations, the headband 110 may be manufactured from any material, or combination of material, suitable for use as a headband.

As shown in FIG. 1, in some implementations, a curved bridle 114 may extend between the first mounting bracket 120a and the second mounting bracket 120b. In some implementations, one or more wires may be secured on and/or supported by the curved bridle 114. In some implementations, heat shrink tubing may be used to secure the one or more wires to the curved bridle 114. In some implementations, the one or more wires may be configured to conductively connect the first mounting bracket 120a and the second mounting bracket 120b to, at least, the first power source 162 (see, e.g., FIG. 5).

Figures 2A, 2B:
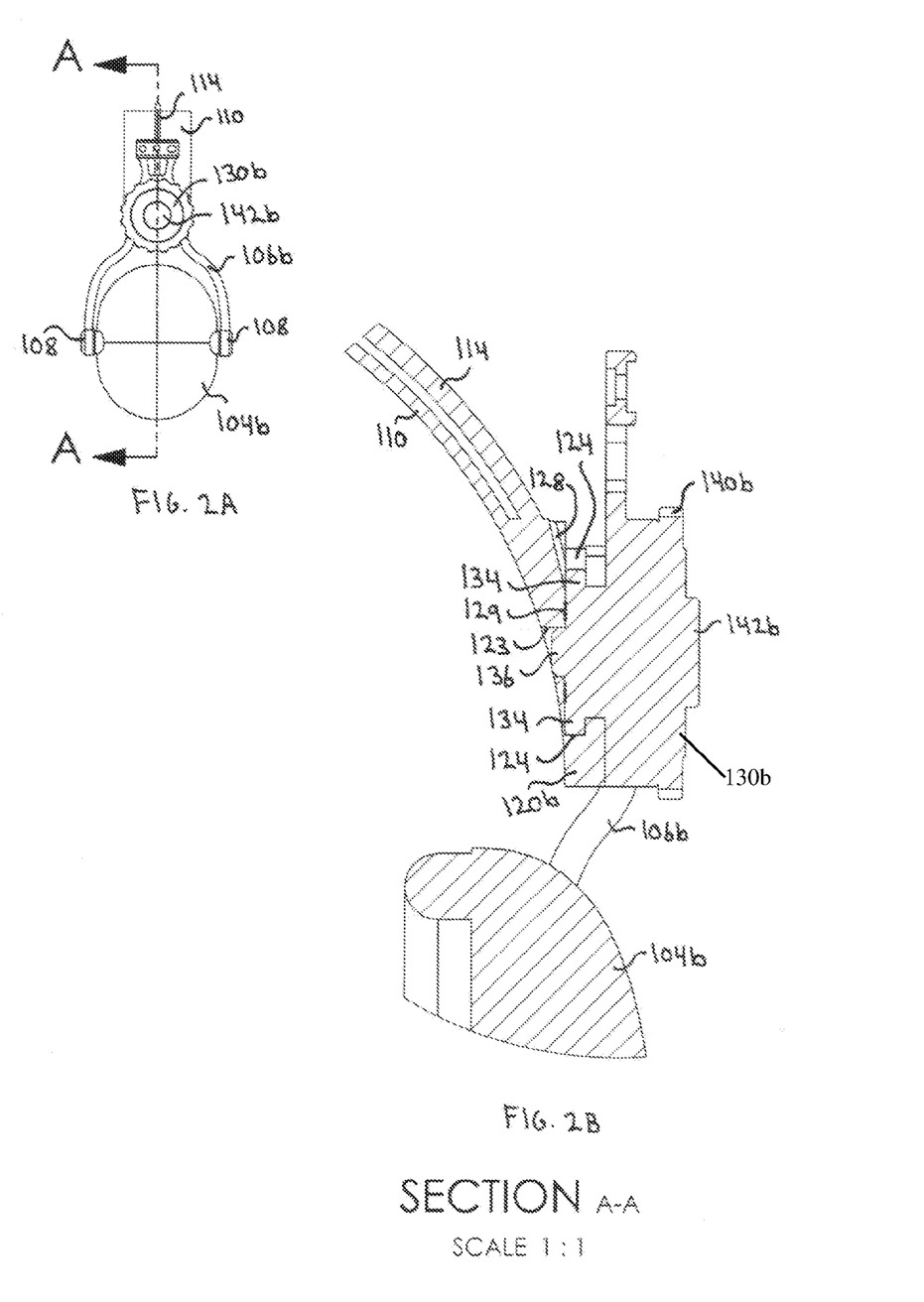
FIG. 2A illustrates a side view of the electronic headset shown in FIG. 1
FIG. 2B illustrates a cross-sectional view of the electronic headset taken along lines A-A of FIG. 2A.
Figure 3B:
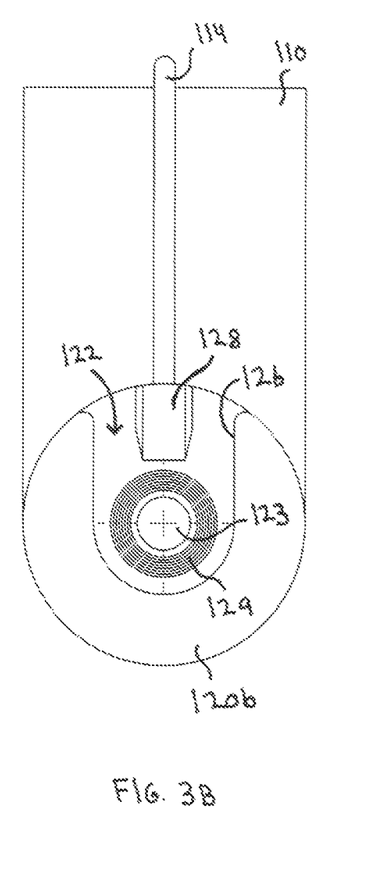
Figure 4:
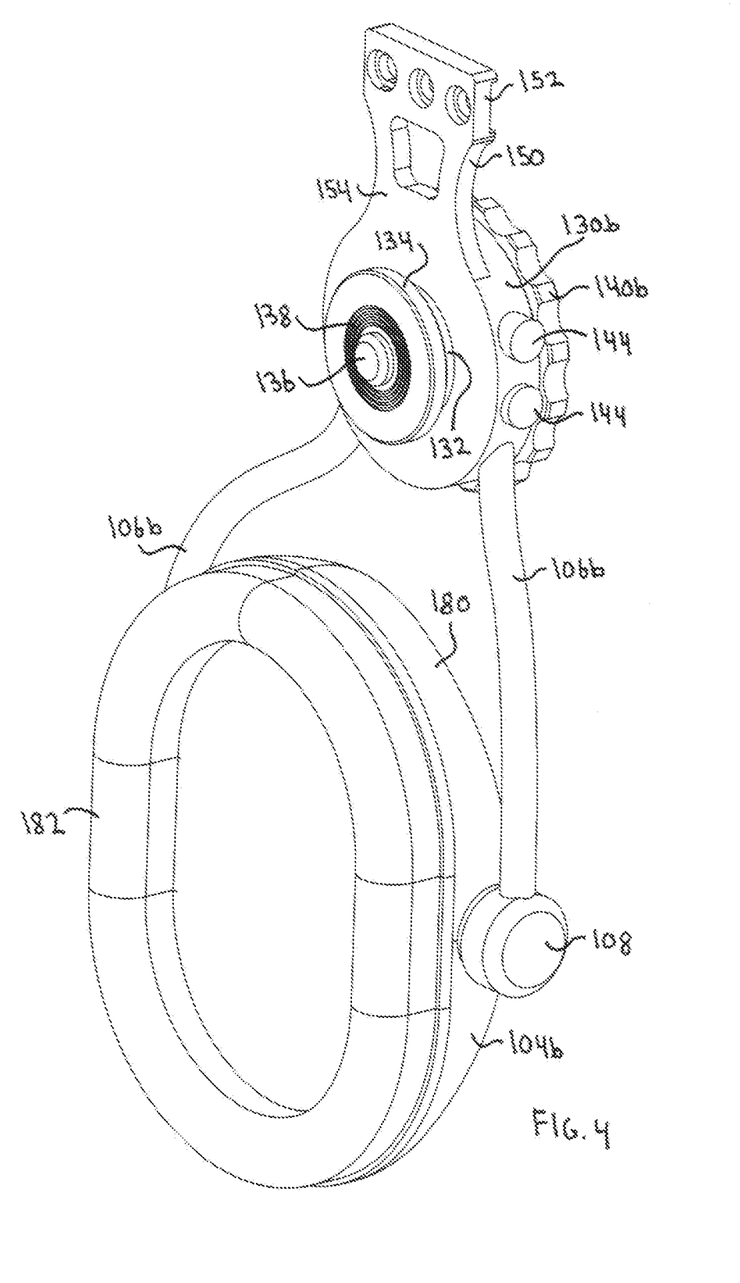
FIG. 4 illustrates an example earcup mounting hub according to the principles of the present disclosure.

As shown in FIGS. 3B and 4, in some implementations, each mounting bracket 120a, 120b on the headband 110 may comprise a pocket 122 configured to receive the circular flange 134 extending from the shaft 132 of a mounting hub 130a, 130b. In some implementations, the pocket 122 of each mounting bracket 120a, 120b may include a recessed interior groove 124 and a U-shaped channel 126 configured to receive the circular flange 134 and shaft 132, respectively, of a mounting hub 130a, 130b (see, e.g., FIGS. 2B and 3B). In this way, a mounting hub 130a, 130b may be removably and/or rotatably coupled to a mounting bracket 120a, 120b of the electronic headset 100.

In some implementations, the recessed interior groove 124 of a pocket 122 of a mounting bracket 120a, 120b may be configured to match the contour of the circular flange 134 of the mounting hub 130a, 130b. In this way, the circular flange 134 may be able to freely rotate within the pocket 122.

Figure 3C:
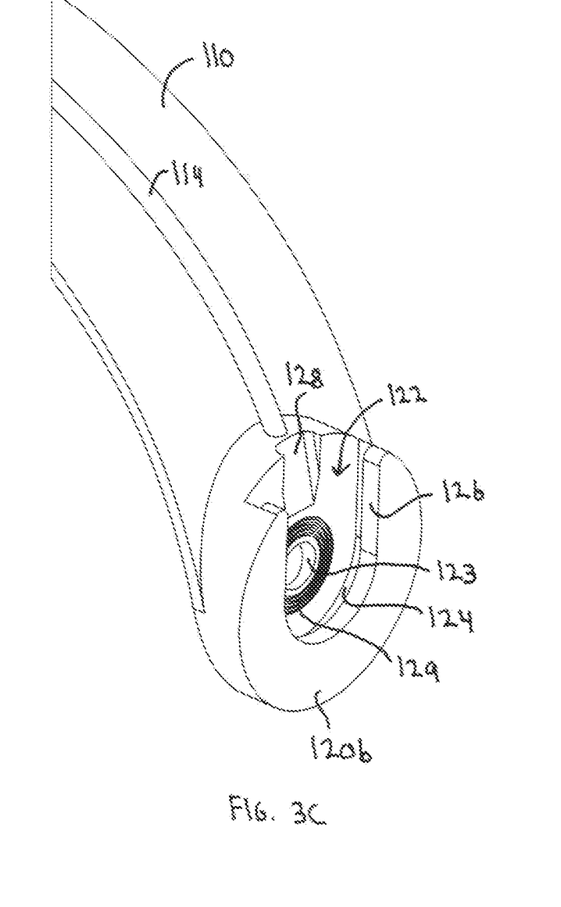

As shown in FIGS. 3B and 3C, in some implementations, each mounting bracket 120a, 120b may include a ramp 128 positioned within the pocket 122 thereof.

In some implementations, as the circular flange 134 of a mounting hub 130a, 130b is being inserted into the pocket 122 of a mounting bracket 120a, 120b, the ramp 128 may gradually compress the spring-loaded pin 136 into the cylindrical shaft 132 of the mounting hub 130a, 130b (not shown). In some implementations, when the circular flange 134 of the mounting hub 130a, 130b has been seated in the pocket 122 of a mounting bracket 120a, 120b, the spring-loaded pin 136 is placed into alignment with, and extends into, a cylindrical bore 123 that extends through the mounting bracket 120a, 120b (see, e.g., FIG. 2B). In this way, the spring-loaded pin 136 may keep the mounting hub 130a, 130b seated in the pocket 122 of the mounting bracket 120a, 120b and allow it to rotate therein (see, e.g., FIG. 1).

As shown in FIG. 3B, in some implementations, there may be a split construction slip ring contact 129 positioned about the cylindrical bore 123 in the pocket 122 of each mounting bracket 120a, 120b. In some implementations, the split construction slip ring contact 129 may be configured to conductively interface with the spring pin contacts 138 positioned about the spring-loaded pin 136 extending from the face of the circular flange 134 of each mounting hub 130a, 130b (see, e.g., FIGS. 2B and 4).

As shown in FIGS. 1 and 4, in some implementations, each earcup mounting hub 130a, 130b may include a circular flange 134 extending from a shaft 132 configured to be received within the pocket 122 of a mounting bracket 120a, 120b, an adjustment knob 140a, 140b, a release button 142a, 142b, and a wire form 106a, 106 having two arms configured to secure an earcup 104a, 104b therebetween.

As shown in FIG. 4, in some implementations, the shaft 132 may have a cylindrical profile and extend from a backside of a mounting hub 130a, 130b. In some implementation, the shaft 132 of a mounting hub 130*a*, 130*b* may include a bore therein into which the spring-loaded pin 136 may slide when being depressed. In some implementations, the circular flange 134 may radially extend from a distal end of the shaft 132. In some implementations, the circular flange 134 may be larger in diameter than the shaft 132 (see, e.g., FIG. 4).

In some implementations, each adjustment knob 140*a*, 140*b* may be configured to move the associated wire form 106*a*, 106*b* and earcup 104*a*, 104*b* between, at least, a first position and a second position of use. In some implementations, the first position of use positions an earcup 104*a*, 104*b* away from the ear of the user. In some implementations, the second position of use positions an earcup 104*a*, 104*b* to abut and seal to a user's head around the ear. In some implementations, each adjustment knob 140*a*, 140*b* may include a camming surface thereon configured to interact with the spring biased wire form 106*a*, 106*b* of a mounting hub 130*a*, 130*b*. In this way, an adjustment knob 140*a*, 140*b* may be used to gradually move an earcup 104*a*, 104*b* between the first position and the second position of use.

As shown in FIGS. 1 and 4, in some implementations, each release button 142*a*, 142*b* may be configured to retract the spring-loaded pin 136 into the shaft 132 of the mounting hub 130*a*, 130*b*. In this way, the circular flange 134 of a mounting hub 130*a*, 130*b* may be removed from the pocket 122 of a mounting bracket 120*a*, 120*b* thereby disconnecting the mounting hub 130*a*, 130*b* from the mounting bracket 120*a*, 120*b*.

In some implementations, the spring-loaded pin 136 may comprise a cylindrical body having an annular chamfer about the protruding end (see, e.g., FIG. 4). In some implementations, the spring-loaded pin 136 may not have an annular chamfer on the protruding end of the cylindrical body.

As shown in FIG. 4, in some implementations, the distal end of each arm of a wire form 106*a*, 106*b* may include an adaptor 108 thereon. In some implementations, each adapter 108 may be configured to connect to a pivot connection located on each side of an earcup 104*a*, 104*b* (see, e.g., FIG. 1). In this way, each earcup 104*a*, 104*b* may be secured between the arms of a wire form 106*a*, 106*b* and/or be more preciously positioned on the side of a wearer's head. In some implementations, the distal end of each arm of a wire form 106*a*, 106*b* may include any adapter thereon that is suitable for securing an earcup of the wearer's choosing therebetween.

As shown in FIG. 4, in some implementations, each mounting hub 130*a*, 130*b* may include two power sockets 144 (or jacks) therein configured to electrically power conductively connected accessories (e.g., a light, a global positioning system (GPS), a thermal imager, a night vision device (NVD), etc.). In some implementations, each power socket 144 may be any suitable jack configured to interface (i.e., connect) with an electrically powered accessory suitable for use with the electronic headset 100. In some implementations, the two power sockets 144 are conductively connected to the spring pin contacts 138 of a mounting hub 130*a*, 130*b* and thereby to the slip ring contact 129 of a connected mounting bracket 120*a*, 120*b* and the one or more wires secured to the bridle 114 of an electronic headset 100. In this way, a connected accessory may be powered. In some implementations, there may be more than two, or less than two, power sockets 144 in each mounting hub 130*a*, 130*b*.

As shown in FIGS. 1 and 4, in some implementations, each mounting hub 130*a*, 130*b* may further comprise an accessory mount 150*a*, 150*b* that includes a mounting interface 152*a*, 152*b* thereon configured to receive therein a portion of an accessory adaptor (e.g., a MIL-STD-1913 rail piece) to which an accessory (e.g., a light, a global positioning system (GPS), etc.) may be attached. In some implementations, an accessory may be configured to secure directly to a mounting interface 152*a*, 152*b* without an accessory adaptor. The general features and advantages of the mounting interface 152*a*, 152*b* and compatible accessory adapters are described in U.S. Pat. No. 9,488,446, filed on Aug. 12, 2014, entitled "MULTIPLE ACCESSORY GUN MOUNT", by Trent Zimmer, which is also owned by the present applicant and is hereby expressly incorporated by reference as if fully set forth herein.

As shown in FIG. 1, in some implementations, the body 154 of an accessory mount 150*a*, 150*b* may be configured to position the mounting interface 152*a*, 152*b* thereon away from (e.g., above) the mounting hub 130*a*, 130*b*. In some implementations, each accessory mount 150*a*, 150*b* may be removably coupled to a mounting hub 130*a*, 130*b*. In some implementations, the cant of each accessory mount 150*a*, 150*b* relative to the headband 110 may be adjustable. In this way, for example, a user may adjust the direction that an attached accessory, for example a light, is pointing.

In some implementations, a mounting hub 130*a*, 130*b* may not include an accessory mount 150*a*, 150*b* thereon.

As shown in FIG. 1, in some implementations, each earcup 104*a*, 104*b* may include a rigid backing 180*a*, 180*b* and cushioned earpads 182*a*, 182*b* that may be configured to encompass and surround the ear of a user. In some implementations, each earcup 104*a*, 104*b* may be configured to abut and seal to a user's head around their ears. In this way, the earcups 104 may be configured so that vibrations and sound waves have to travel through the earcups 104. In some implementations, the earcups 104 may be passive and not require any electronic aid to provide hearing protection.

In some implementations, each earcup 104*a*, 104*b* may be configured to include an electronic sound dampening device mounted thereon (not shown, but well known to those of ordinary skill in the art). An example sound dampening device may include a microphone positioned on an outer surface of an earcup 104*a*, 104*b*. The microphone may be configured to pick up ambient sounds from around the user and transmit the ambient sounds to a sound compression or suppression circuit mounted inside an earcup 104*a*, 104*b* that filters out or suppresses sounds above a predetermined decibel level. Sounds lower than the set level are then transmitted to earphones inside the earcups 104 so that the user of the electronic headset 100 can hear non-damaging sounds in the surrounding environment (e.g., people talking nearby). An example sound circuit can be adjusted by a volume switch or knob mounted to an earcup 104*a*, 104*b* and conductively coupled to the sound dampening device. In some implementations, the sound dampening device may be conductively coupled to the electronic circuit 160 via the conductive interface that exists between a coupled mounting bracket 120*a*, 120*b* and mounting hub 130*a*, 130*b*.

FIG. 5 shows an example implementation of an electronic circuit 160 used to power electronic earcups 104 and/or other electrically powered accessories conductively coupled to the electronic headset 100. In some implementations, the electronic circuit 160 may comprise a first power source 162 (e.g., a battery pack) conductively connected to the first earcup 104*a* and/or the second earcup 104*b* via the conductive interface that exist between a coupled mounting bracket 120*a*, 120*b* and mounting hub 130*a*, 130*b*. In some implementations, an electrically powered accessory may be conductively connected to the first power source 162 via the power socket(s) 144 in each mounting hub 130a, 130b. In some implementations, the first power source 162 may also be configured to act as a junction and provide one or more additional power sockets 144 to which electrically powered accessories may be conductively coupled (see, e.g., FIG. 5).

In some implementations, the housing of the first power source 162 may be configured to mount on, or be permanently affixed to, the headband 110 of the electronic headset 100.

As shown in FIG. 5, in some implementations, the electronic circuit 160 may further comprise a second power source 164 (e.g., a battery pack). In some implementations, the second power source 164 may be conductively connected to the circuit (e.g., 160) to which the first power source 162 is conductively connected. In some implementations, the electronic circuit 160 may not include a second power source 164.

In some implementations, the housing of the second power source 164 may be configured to mount on, or be permanently affixed to, the headband 110 of the electronic headset 100. In some implementations, the second power source 164 may be connected to the electronic circuit 160 of an electronic headset 100 via a suitably configured electronic cable. In this way, the second power source may be remotely positioned relative to the electronic headset 100 (e.g., carried in the pocket of a wearer, positioned on a helmet, etc.).

Although not shown in the drawings, it will be understood that suitable wiring connects the electrical components (e.g., the first power source 162, the earcups 104, the power socket(s) 144, and/or the second power source 164) of the electronic headsets 100, 200 disclosed herein.

Figure 6:
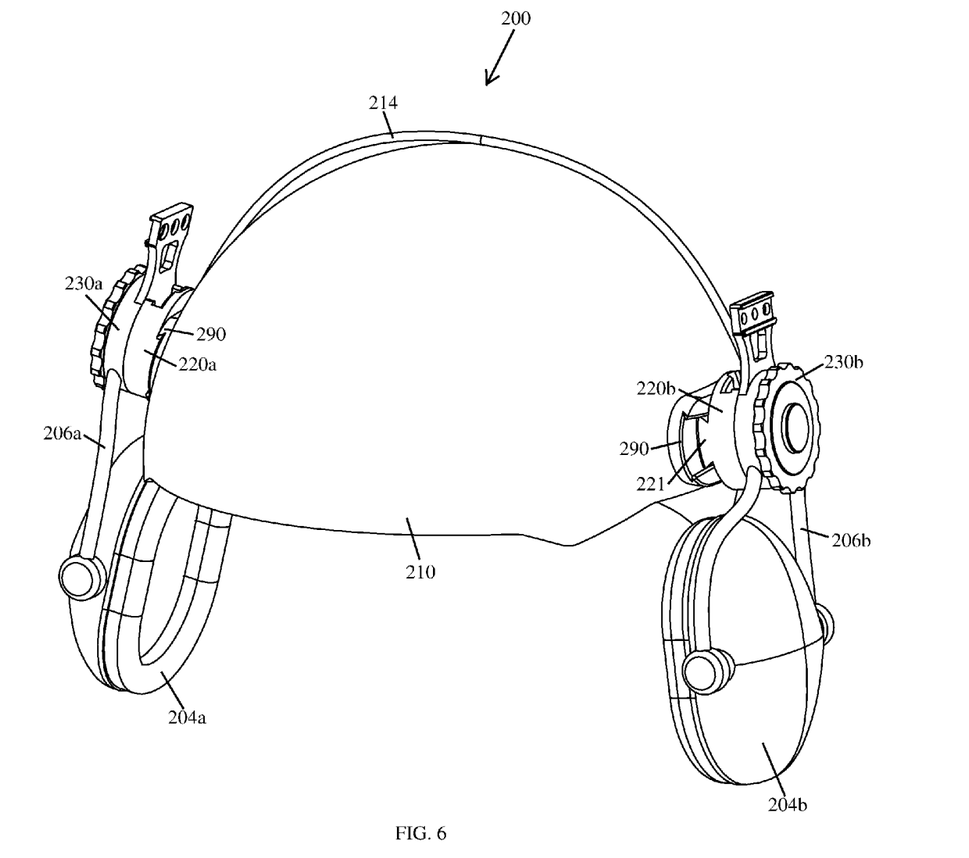
FIG. 6 illustrates another example implementation of the electronic headset according to the principles of the present disclosure.

FIG. 6 illustrates another example implementation of the electronic headset 200 in accordance with the present disclosure. In some implementations, the electronic headset 200 is similar to the electronic headset 100 discussed above except for the mounting brackets 220a, 220b which may be configured for use with a helmet 210, instead of a headband. In some implementations, each mounting bracket 220a, 220b may be secured to a suitable interface (e.g., a rail system) positioned on each side of the helmet 210 (see, e.g., FIG. 6). In some implementations, the mounting brackets 220 of the electronic headset 200 may be configured to attach to an Ops-Core ARC rail, Crye Precision AirFrame rail, Team Wendy, and/or MTek type rail systems, well known in the prior art.

As shown in FIG. 6, in some implementations, each mounting bracket 220a, 220b may include a back plate 221 configured to be received within the rail channel of a helmet rail system 290. In some implementations, the sides of the back plate 221 may be slanted and configured to interface with the slanted walls of the rail channel (see, e.g., FIG. 6). In some implementations, the sides of the back plate 221 may be constructed as a male portion of a dovetail joint. In this way, when the back plate 221 of a mounting bracket 220a, 220b is inserted into the rail channel (e.g., the female portion of a dovetail joint) of a helmet rail system 290 a secure connection may be achieved (see, e.g., FIG. 6). In some implementations, the back plate 221 may have any shape suitable for being received within the rail channel of a helmet mounted rail system.

In some implementations, the back plate 221 may be adjustably secured to the rear side of a mounting bracket 220a, 220b. In this way, the back plate 221 may be used to clamp a mounting bracket 220a, 220b to the rail channel of a helmet rail system 290.

In some implementations, the mounting brackets 120, 220 and the earcup mounting hubs 130 may be manufactured from an impact resistant polymer. In some implementations, the mounting brackets 120, 220 and the earcup mounting hubs 130 may be manufactured from an aluminum alloy. In some implementations, the mounting brackets 120, 220 and the earcup mounting hubs 130 may be manufactured from any material, or combination of materials, known to those of ordinary skill in the art.

Reference throughout this specification to "an embodiment" or "implementation" or words of similar import means that a particular described feature, structure, or characteristic is included in at least one embodiment of the present invention. Thus, the phrase "in some implementations" or a phrase of similar import in various places throughout this specification does not necessarily refer to the same embodiment.

Many modifications and other embodiments of the inventions set forth herein will come to mind to one skilled in the art to which these inventions pertain having the benefit of the teachings presented in the foregoing descriptions and the associated drawings.

The described features, structures, or characteristics may be combined in any suitable manner in one or more embodiments. In the above description, numerous specific details are provided for a thorough understanding of embodiments of the invention. One skilled in the relevant art will recognize, however, that embodiments of the invention can be practiced without one or more of the specific details, or with other methods, components, materials, etc. In other instances, well-known structures, materials, or operations may not be shown or described in detail.

While operations are depicted in the drawings in a particular order, this should not be understood as requiring that such operations be performed in the particular order shown or in sequential order, or that all illustrated operations be performed, to achieve desirable results.

The invention claimed is:

1. An electronic headset configured to position an earcup over each ear of a wearer, the electronic headset comprising:
   a headband having a first end and a second end, the headband is configured to fit on the crown of the wearer's head;
   a power source, the power source is secured to the headband;
   a first mounting bracket and a second mounting bracket, the first mounting bracket is positioned on the first end of the headband and the second mounting bracket is positioned on the second end of the headband, the first mounting bracket and the second mounting bracket are conductively connected to the power source; and
   a first earcup mounting hub and a second earcup mounting hub, the first earcup mounting hub is conductively coupled to the first mounting bracket and the second earcup mounting hub is conductively coupled to the second mounting bracket;
   wherein the first earcup mounting hub comprises a wire form configured to secure a first earcup thereto and the second earcup mounting hub comprises a wire form configured to secure a second earcup thereto.

2. The electronic headset of claim 1, wherein the first earcup mounting hub is configured to removably couple to the first mounting bracket and the second earcup mounting hub is configured to removably couple to the second mounting bracket.

3. The electronic headset of claim 2, wherein the first mounting bracket and the second mounting bracket each comprise a pocket; wherein the first earcup mounting hub and the second earcup mounting hub each comprise a shaft that extends from a backside thereof, each shaft includes a circular flange radially extending from a distal end thereof; and wherein the pocket of the first mounting bracket is configured to removably receive therein the circular flange of the first earcup mounting hub and the pocket of the second mounting bracket is configured to removably receive therein the circular flange of the second earcup mounting hub.

4. The electronic headset of claim 3, wherein the pocket of each mounting bracket further comprises an electrical contact therein and each earcup mounting hub further comprises an electrical contact on a face of the circular flange thereof; and wherein the electrical contact of the first mounting bracket and the second mounting bracket is configured to conductively interface with the electrical contact of the first earcup mounting hub and the second earcup mounting hub, respectively, when coupled together.

5. The electronic headset of claim 4, wherein the electrical contact in the pocket of each mounting bracket is a split construction slip ring contact and the electrical contact on the face of the circular flange of each earcup mounting hub is at least one spring pin contact.

6. The electronic headset of claim 3, wherein the first earcup mounting hub and the second earcup mounting hub each further comprise a spring-loaded pin that extends from the shaft thereof; wherein the first mounting bracket and the second mounting bracket each further comprise a cylindrical bore in the pocket thereof; and wherein the spring-loaded pin of the first earcup mounting hub and the second earcup mounting hub is configured to extend into the cylindrical bore of the first mounting bracket and the second mounting bracket, respectively, when placed into alignment therewith.

7. The electronic headset of claim 6, wherein the pocket of each mounting bracket further comprises an electrical contact that is positioned about the cylindrical bore and each earcup mounting hub further comprises an electrical contact on a face of the circular flange that is positioned about the spring-loaded pin extending from the shaft thereof; and wherein the electrical contact of the first mounting bracket and the second mounting bracket is configured to conductively interface with the electrical contact of the first earcup mounting hub and the second earcup mounting hub, respectively, when coupled together.

8. The electronic headset of claim 7, wherein the electrical contact in the pocket of each mounting bracket is a split construction slip ring contact and the electrical contact on the face of the circular flange of each earcup mounting hub is at least one spring pin contact.

9. The electronic headset of claim 1, further comprising a curved bridle that extends between the first mounting bracket and the second mounting bracket, at least one wire conductively connecting the power source to the first mounting bracket and the second mounting bracket is supported by the curved bridle.

10. The electronic headset of claim 4, further comprising a curved bridle that extends between the first mounting bracket and the second mounting bracket, at least one wire conductively connecting the power source to the first mounting bracket and the second mounting bracket is supported by the curved bridle.

11. The electronic headset of claim 7, further comprising a curved bridle that extends between the first mounting bracket and the second mounting bracket, at least one wire conductively connecting the power source to the first mounting bracket and the second mounting bracket is supported by the curved bridle.

12. The electronic headset of claim 1, wherein each earcup mounting hub further comprises at least one power socket that is configured to power a conductively connected electrically powered accessory, the at least one power socket is conductively connected to the power source.

13. The electronic headset of claim 12, wherein the power source comprises at least one power socket that is configured to power a conductively connected electrically powered accessory.

14. The electronic headset of claim 4, wherein each earcup mounting hub further comprises at least one power socket that is configured to power a conductively connected electrically powered accessory, the at least one power socket of each earcup mounting hub is conductively connected to the electrical contact on the face of the circular flange.

15. The electronic headset of claim 7, wherein each earcup mounting hub further comprises at least one power socket that is configured to power a conductively connected electrically powered accessory, the at least one power socket of each earcup mounting hub is conductively connected to the electrical contact on the face of the circular flange.

16. The electronic headset of claim 1, wherein the power source comprises at least one power socket that is configured to power a conductively connected electrically powered accessory.

17. An electronic headset configured for use with a helmet and to position an earcup over each ear of a wearer, the electronic headset comprising:
   a power source, the power source is secured to the helmet;
   a first mounting bracket and a second mounting bracket, the first mounting bracket is configured to secure to an interface positioned on a first side of the helmet and the second mounting bracket is configured to secure to an interface positioned on a second side of the helmet, the first mounting bracket and the second mounting bracket are conductively connected to the power source; and
   a first earcup mounting hub and a second earcup mounting hub, the first earcup mounting hub is conductively coupled to the first mounting bracket and the second earcup mounting hub is conductively coupled to the second mounting bracket;
   wherein the first earcup mounting hub comprises a wire form configured to secure a first earcup thereto and the second earcup mounting hub comprises a wire form configured to secure a second earcup thereto.

18. The electronic headset of claim 17, wherein the first mounting bracket includes a back plate configured to be received within a channel of the interface positioned on the first side of the helmet and the second mounting bracket includes a back plate configured to be received within a channel of the interface positioned on the second side of the helmet.

19. The electronic headset of claim 17, wherein the first earcup mounting hub is configured to removably couple to the first mounting bracket and the second earcup mounting hub is configured to removably couple to the second mounting bracket.

20. The electronic headset of claim 19, wherein the first mounting bracket and the second mounting bracket each comprise a pocket; wherein the first earcup mounting hub and the second earcup mounting hub each comprise a shaft that extends from a backside thereof, each shaft includes a circular flange radially extending from a distal end thereof; and wherein the pocket of the first mounting bracket is configured to removably receive therein the circular flange of the first earcup mounting hub and the pocket of the second mounting bracket is configured to removably receive therein the circular flange of the second earcup mounting hub.

21. The electronic headset of claim 20, wherein the pocket of each mounting bracket further comprises an electrical contact therein and each earcup mounting hub further comprises an electrical contact on a face of the circular flange thereof; and wherein the electrical contact of the first mounting bracket and the second mounting bracket is configured to conductively interface with the electrical contact of the first earcup mounting hub and the second earcup mounting hub, respectively, when coupled together.

22. The electronic headset of claim 21, wherein the electrical contact in the pocket of each mounting bracket is a split construction slip ring contact and the electrical contact on the face of the circular flange of each earcup mounting hub is at least one spring pin contact.

23. The electronic headset of claim 20, wherein the first earcup mounting hub and the second earcup mounting hub each further comprise a spring-loaded pin that extends from the shaft thereof; wherein the first mounting bracket and the second mounting bracket each further comprise a cylindrical bore in the pocket thereof; and wherein the spring-loaded pin of the first earcup mounting hub and the second earcup mounting hub is configured to extend into the cylindrical bore of the first mounting bracket and the second mounting bracket, respectively, when placed into alignment therewith.

24. The electronic headset of claim 23, wherein the pocket of each mounting bracket further comprises an electrical contact that is positioned about the cylindrical bore and each earcup mounting hub further comprises an electrical contact on a face of the circular flange that is positioned about the spring-loaded pin extending from the shaft thereof; and wherein the electrical contact of the first mounting bracket and the second mounting bracket is configured to conductively interface with the electrical contact of the first earcup mounting hub and the second earcup mounting hub, respectively, when coupled together.

25. The electronic headset of claim 24, wherein the electrical contact in the pocket of each mounting bracket is a split construction slip ring contact and the electrical contact on the face of the circular flange of each earcup mounting hub is at least one spring pin contact.

26. The electronic headset of claim 17, further comprising a curved bridle that extends between the first mounting bracket and the second mounting bracket, at least one wire conductively connecting the power source to the first mounting bracket and the second mounting bracket is supported by the curved bridle.

27. The electronic headset of claim 17, wherein each earcup mounting hub further comprises at least one power socket that is configured to power a conductively connected electrically powered accessory, the at least one power socket is conductively connected to the power source.

28. The electronic headset of claim 17, wherein the power source comprises at least one power socket that is configured to power a conductively connected electrically powered accessory.

* * * * *